United States Patent [19]

Suzuki et al.

[11] Patent Number: 4,704,112
[45] Date of Patent: Nov. 3, 1987

[54] FACING FOR ABSORPTIVE ARTICLES AND PROCESS FOR MAKING IT

[75] Inventors: Migaku Suzuki, Kawanoe; Satoshi Nozaki, Ehime, both of Japan

[73] Assignee: Uni-Charm Corporation, Ehime, Japan

[21] Appl. No.: 825,611

[22] Filed: Feb. 3, 1986

[51] Int. Cl.⁴ .............................................. A61F 13/16
[52] U.S. Cl. .................................... 604/378; 604/379; 604/380
[58] Field of Search ................................. 604/378-383

[56] References Cited

U.S. PATENT DOCUMENTS 3,056,406 10/1962 Ness ...................................... 604/377
3,088,463 5/1963 Harmon .............................. 604/383
4,323,069 4/1982 Ahr et al. ............................ 604/378

Primary Examiner—C. Fred Rosenbaum
Assistant Examiner—Sherri E. Vinyard
Attorney, Agent, or Firm—Fred Philpitt

[57] ABSTRACT

Facing for absorptive articles comprising non-woven fabric having two layers of different fibre-compositions, i.e., a first layer defining a surface to be in contact with the wearer's skin and having a pattern of apertures, and a second layer defined a rear side with respect to said surface and having no aperture.

Process for making said facing comprising steps forming said first layer by subjecting fibrous web to high velocity water jet treatment on a support carring thereon aperture formation element, forming said second layer by subjecting fibrous web to said treatment or heat fusion treatment, and simultaneously combining said first layer integrally with said second layer with either of said treatments (FIG. 1).

10 Claims, 7 Drawing Figures

FACING FOR ABSORPTIVE ARTICLES AND PROCESS FOR MAKING IT

(TECHNICAL FIELD)

The present invention relates to facing for absorptive articles used to handle body fluid such as disposable diapers, inconsistence pads and sanitary napkins.

(BACKGROUND OF INVENTION)

As facing for such absorptive articles, there have been adopted the following:

(a) non-woven fabric composed substantially of hydrophilic fibres:

This is composed substantially of hydrophilic fibres such as rayon fibres so as to improve a permeability for body fluid. However, its relatively high permeability results in increased residue of body fluid on the surface of non-woven fabric after body fluid has permeated the fabric and said surface in contact with the wearer's skin remains discomfortably wetted.

(b) two-layered non-woven fabric comprising an upper layer of hydrophobic fibres and a lower layer of hydrophilic fibres:

Although the problem encountered by said (a) has been solved to some extent by incorporation of hydrophobic fibres as the upper layer, the effect is largely limited by a requirement that the upper layer should be formed as thinly as possible to maintain a desired permeability for body fluid. Thus, such concept can not be considered a satisfactory solution.

(c) non-woven fabric composed of hydrophobic fibres only, and provided with an agent imparting a hydrophilic nature thereto:

Problems of said (a) and (b) are solved by (c) so far as a first contact with body fluid is concerned. Said hydrophilic nature imparting agent is washed away as body fluid permeates the non-woven fabric for the first time and it becomes difficult later for body fluid to permeate the non-woven fabric repeatedly.

(d) soft thermoplastic film having a plurality of apertures formed therein by a thermoforming process, and a fibrous layer bonded by adhesive agent to its underside:

Problems of said (a), (b) and (c) are substantially solved by this arrangement. However, the area other than said apertures has no breathability and no permeability for humidity generated on the wearer's skin, so that the latter becomes musty. Further, such facing has no fabric touch and gives the wearer's skin discomfortably cold feel particularly in a cold season.

Characteristics desired for the facing of such absorptive articles include a high permeability, no wet feeling remaining on the facing after permeation of body fluid, i.e., a dry feel to the wearer's skin, being free from rewetting with body fluid occurring under a pressure upon the facing after body fluid has permeated the facing, and a comfortable feeling when worn.

Said prior art has never been able to adjust or control these characteristics which conflict with one another so that the respective characteristics may be simultaneously achieved.

A principal object of the present invention is, therefore, to provide an improved facing for absorptive articles so as to satisfy the requirements for the above characteristics simultaneously.

SUMMARY OF THE INVENTION

The present invention broadly resides in a facing for absorptive articles comprising a combined non-woven fabric having two layers of different fibre-compositions, i.e., a first layer defining a surface to be in contact with the wearer's skin and a second layer defining a rear side with respect to said surface, said first layer being composed of hydrophobic fibres in an amount of 70 to 100% by weight and hydrophilic fibres in an amount of 0 to 30% by weight, having a basic weight of $15 g/m^2$ at least and a pattern of apertures with the area of 0.29 to 30 $mm^2$ formed in said first layer at a ratio of 10 to 50% with respect to its total area; and said second layer being composed of hydrophilic fibres in an amount of 50 to 100% by weight and hydrophilic fibres in 0 to 50% by weight, having a basic weight of 5 to 50 $g/m^2$ and no apertures.

The present invention resides also in a process for making said facing, said process comprising steps of subjecting fibrous webs to high velocity water jet to obtain said first layer and said second layer, respectively, and then bonding these two layers to each other, or subjecting said fibrous web to said high velocity water jet to obtain said first layer while fusing fibres of an associated fibrous web together to form said second layer and bonding these two layers to each other.

DETAILED DESCRIPTION OF INVENTION:

Above-mentioned and other features of the present invention will be apparent from the following description in reference with embodiments as shown by the accompanying drawing.

Figure 1:
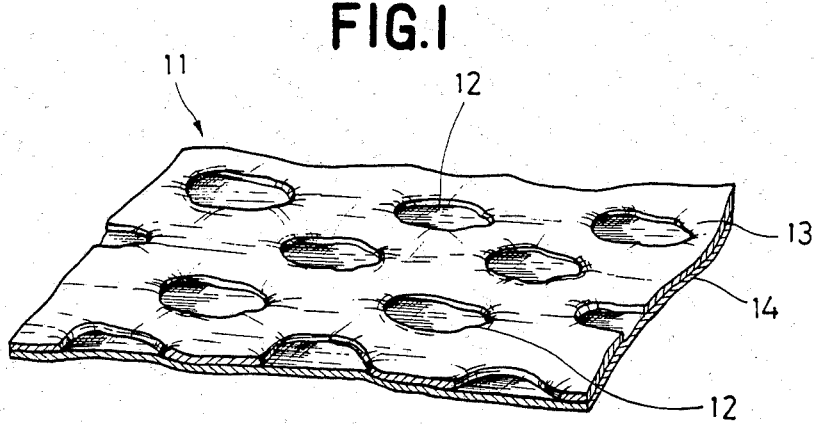
FIG. 1 is a partially enlarged perspective view schematically illustrating facing according to the present invention.
Figure 2:
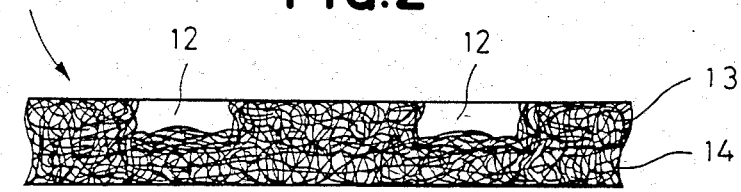
FIG. 2 is a partially enlarged sectional view schematically illustrating the first layer and the second layer of said facing formed by high velocity water jet process and then bonded together.
Figure 3:
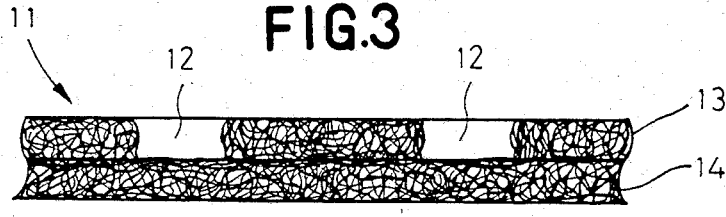
FIG. 3 is a partially enlarged sectional view schematically illustrating said first and second layers after said bonding has been achieved by heat treatment.

As seen in FIGS. 1 through 3, facing 11 has a pattern of apertures 12 and comprises an integrally combined nonwoven fabric having a first layer 13 defining surface to be in contact with the wearer's skin and a second layer 14 defining a rear side with respect to said surface.

To achieve the object of the present invention, the first layer 13 should have a fibrous composition of hydrophobic fibres in an amount of 100% by weight, a basic weight of 15 $g/m^2$ or more, a density of 0.03 $g/cm^3$ or more, preferably of 0.1 to 0.3 $g/cm^3$, and a denier of 0.2 to 2, preferably of 0.5 to 1. However, the presence of hydrophilic fibres would not noticeably affect the desired quality and the maximum acceptable content thereof would be 30% by weight. Similarly to achieve the object of the present invention, the second layer 14 should be composed of hydrophilic fibres in an amount of 100% by weight, and have a basic weight of 5 to 50 g/cm$^2$, a density of 0.01 to 0.2 g/cm$^3$, preferably of 0.02 to 0.07 g/cm$^3$ and a denier of 0.7 to 15, preferably of 3 to 8. Depending on the size of each aperture 12 formed in the first layer 13, the ratio of the area of the apertures with respect to the total area of said first layer 13, said density of the second layer 14, etc., the presence of hydrophobic fibres in an amount up to 50% by weight would not affect the desired quality but rather a suitable content of hydrophobic fibres would advantageously hold a desired elasity under a wet condition. The apertures 12 formed elliptically in the first layer 13, to achieve the object of the invention, should have an area from 0.29 to 30 mm$^2$, preferably from 0.35 to 11 mm, an aperture ratio from 10 to 60%, preferably from 20 to 50%, and should be formed by pushing or thrusting i.e., moving fibres aside without partially cutting off the fibres of the first layer 13 for improvement of strength, feel and appearance. It should be noted here that the configuration of the apertures is not limitted to that as shown in FIG. 1.

The first layer 13 is preferably a non-woven fabric in which individual fibres are entangled with one another. Such non-woven fabric is obtained by subjecting a web of loose fibres disposed in random relationship with one another as initial material for non-woven fabric to high velocity water jet treatment so as to achieve a desired fibre entanglement on a support. The second layer 14 is also preferably non-woven fabric in which individual fibres are mutually entangled but no apertures are formed. This does not exclude a possibility that the second layer 14 may be formed by fusing individual fibres together through the heat treatment. In the latter case, all or a part of the hydrophobic fibres contained in the second layer 14 preferably comprises thermo-fusive fibres. The optimal process for formation of the first layer 13 and the second layer 14 in the form of non-woven fabric and integrally combining these two components comprises, in one embodiment, steps of subjecting fibrous web to be formed into the first layer 13 to said treatment so as to achieve a desired fibre entanglement, then placing the other fibrous web to be formed into the second layer 14 upon said first layer 13, and subjecting the last-mentioned fibrous web placed upon said first layer 13 to said treatment again so as to achieve the similar fibre entanglement not only among individual fibres of said second layer 14 but also with those of said first layer 13. In another embodiment, said fibrous web to be formed into the second layer 14 and containing therein said thermo-fusive fibres is placed upon the first layer 13 formed in accordance with the treatment as adopted in the first embodiment and then this assembly is subjected to said heat treatment so that individual fibres of said fibrous web destined to be formed into the second layer 14 may be fused together not only in this fibrous web but also with individual fibres in the first-mentioned fibrous web destined to be formed into the first layer 13. When the process is implemented in the first-mentioned manner, fibres of the first layer 13 and the second layer 14 are partially mixed and the boundary between these two layers is not clear, as seen in FIG. 2 and, when the process is implemented in the second manner, fibers of the first layer 13 and the second layer 14 are fused together exclusively along a boundary of these two layers, so that this boundary is relatively clear, as seen in FIG. 3.

Formation of the first layer 13 by the fibre entanglement is extremely convenient for the formation of the apertures 12 by distributing fibres aside. Specifically, the fibrous web destined to be formed into the first layer 13 may be subjected to the high velocity water jet treatment as said web travels on the support having therearound aperture formation elements to achieve the desired fibre entanglement and simultaneously to form the apertures as said aperture formation elements distribute fibres aside.

Hydrophobic fibres useful for the first layer 13 include polyester, polypropyrene, polyethylene, acryl, polyurethane fibres, etc. and the second layer 14 may be formed by synthetic fibres such as polyester of which the fibre surface has been imparted with hydrophilic nature, rayon fibres, cotton fibres, etc. Although these may be used independently or in combination, it is rather preferred to form the first layer 13 from polyester fibres and to form the second layer 14 substantially from polyester fibres treated so as to have a hydrophilic nature. Such treatment is preferably achieved by use of the treatment agents obtained, for example, by processes for preparing treatment agents for polyester moldings as disclosed in Japanese Patent Publications Nos. 44 - 2580, 44 - 2581 and 44 - 3967.

The important factors in the present invention as have been numerically specified above will be further considered. The first layer 13 having a basic weight less than 15 g/m$^2$ and a density less than 0.03 g/cm$^3$ could not satisfactorily prevent body fluid from flowing backwards resulting in so-called rewetting effect, the second layer 14 having a basic weight of 50 g/m$^2$ or more and a density of 0.2 g/cm$^3$ or more would decrease the permeability for body fluid, the first layer 13 having the apertures with areas less than 0.29 mm$^2$ and an aperture ratio less than 10% would result in an unacceptably low permeability for body fluid, and the first layer 13 having the apertures 12 with the area of 30 mm$^2$ or larger and an aperture ratio of 60% or higher would cause the second layer 14 to come in direct contact with the wearer's skin through said apertures or would cause body fluid to flow backwards through said apertures and cause a discomfortably wet feel. It should be noted that, although the first layer 13 exhibits no difference in its function even when the basic weight exceeds a range 40 g/m$^2$ or more, such excessive basic weight is economically disadvantageous.

Figure 4:
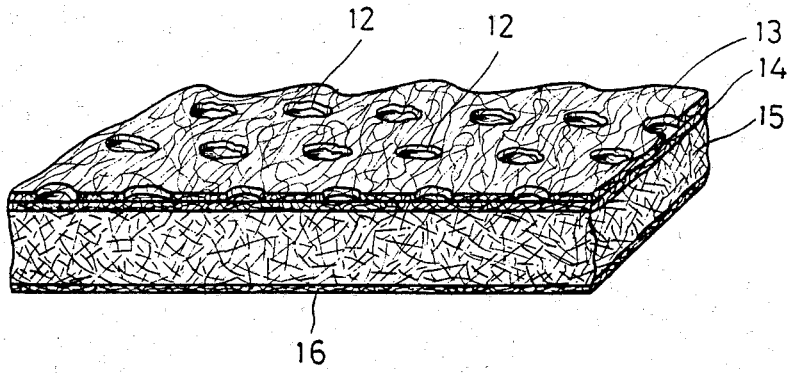
FIG. 4 is a fragmentary perspective view schematically illustrating said facing utilized for absorptive articles.

The facing 11 constructed as has been mentioned above is utilized, as a shown by way of example in FIG. 4, for the absorptive articles such as disposable diaper, inconsistence pad and sanitary napkin which basically comprise an absorbent body 15 substantially made of cotton-like woody pulp carrying on its top said facing 11 with the first layer 13 thereof defining the upper surface and provided on the underside of said absorbent body 15 with a water-impermeable sheet 16 such as plastic film. The rest arrangement in the absorptive articles is similar to that in such articles of the prior art. When body fluid is excreted on a certain spot of the first layer 13 constituting the facing 11 now utilized as the component of the absorptive article, body fluid permeates the second layer 14 through the respective apertures 12 present within said spot and is absorbed by the absorbent body 15. The body fluid thus absorbed in substantially prevented from flowing backwards through the facing 11, since at least 70% by weight of the fibres constituting the first layer 13 is hydrophobic and the apertures 12 are formed with an area of 0.29 mm$^2$ or less in an aperture ratio of 60% or less. The second layer 14 will somewhat swell at the respective apertures 12, depending on the manner in which the first layer 13 is combined with the second layer 14. In such a case the second layer 14 is well behind the surface of the first layer 13, so that the second layer 14 is substantially kept from direct contact with the wearer's skin even when the second layer 14 might be somewhat wet with body fluid. Further, the facing 11 is breathable not only at portions corresponding to the respective apertures 12 but also as a whole, since the facing 11 is formed of fibres wholly entangled with one another or partially fused together.

Figure 5:
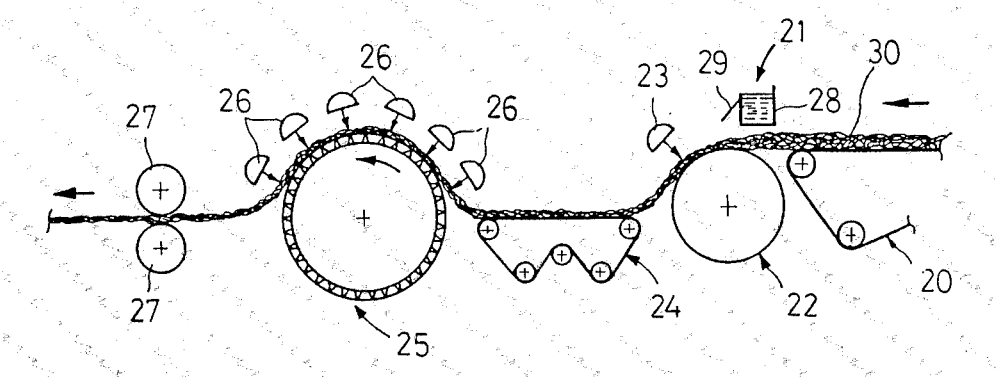
FIG. 5 is a side view schematically illustrating, by way of example, of an apparatus for making said facing by high velocity water jet process.
Figure 6:
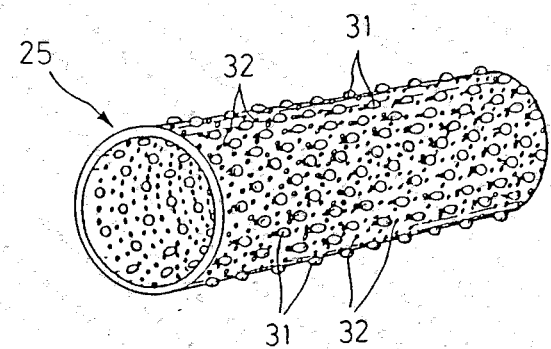
FIG. 6 is a perspective view schematically illustrating a support roll arranged in said apparatus and having therearound aperture forming elements.
Figure 7:
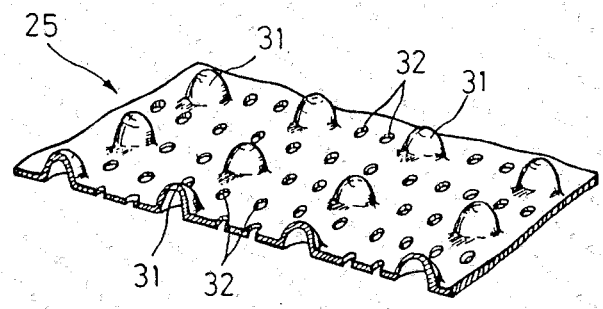
FIG. 7 is a partially enlarged plan view schematically illustrating said support roll.

To obtain the first layer 13 of the non-woven fabric which constitutes the facing according to the present invention, fibres are entangled with one another and the apertures are formed preferably by an apparatus as shown by FIGS. 5 and 6, although a high velocity water jet apparatus of the prior art may be used. The apparatus of FIG. 5 includes a belt conveyor 20, water screen supply means 21, a first support roll 22, water jet means 23, opposed to a periphery of said first support roll 22, another belt conveyor 24, a second support roll 25 carrying therearound aperture formation elements, a plurality of water jet means 26 arranged at predetermined intervals and opposed to the periphery of said second support roll 25, and a pair of squeeze rolls 27. The water screen supply means 21 includes a reservoir 28 adapted to maintain a predetermined quantity of water overflowing it, and a tilting plate 29 along which said predetermined quantity of water continuously flows down, forming a water screen which is supplied over fibrous web 30. Thereby, the fibrous web 30 is effectively prevented from becoming fluffy and maintains its texture so that the fibre entanglement treatment may be effectively achieved. The second support roll 25 is provided in the form of a cylinder having predetermined diameter and length. Said cylinder has a repeating pattern of projections 31 arranged on a smooth peripheral surface of said cylinder at predetermined spacings from one another, and, in the flat area defined among said projections, a plurality of perforations 32 for drainage. Each of said projections 31 is preferably configured so that the apertures 12 may be formed in the fibrous web 30 at a high efficiency and the non-woven fabric thus formed may be readily peeled off from the second support roll 25. To this end, the projection 31 is preferably tapered from its base to its top, for example, in the form of a semi-sphere. The diameter, the area ratio with respect to the peripheral surface of the cylinder and the distribution pattern of the projections 31 substantially correspond to those of the apertures 12 in the first layer 13, and the height of each projection 31 is preferably selected between 0.4 and 10 mm in order that the apertures 12 may be clearly formed in the non-woven fabric. The first support roll 22 preferably includes a plurality of perforations (not shown) for drainage of 0.2 to 1.0 mm in diameter, distributed at predetermined spacings over its peripheral surface at an occupation ratio of 2.5 to 30% with respect to a total area of said peripheral surface. The first support roll 22 and the second support roll 25 include suction means (not shown) therein for suction drainage so that the efficiency of drainage on the outer surfaces of the respective rolls 22, 25 may be promoted. Both the first support roll 22 and the second support roll 25 have predetermined hardnesses so as to assure that the water streams directed from the respective jet means 23, 26 rebound on the roll surfaces of said first and second supports 22, 25, respectively, and these bounding water streams serve again to effect the fibre entanglement. The fibrous web 30 is preliminarily fibre-entanglement treated on the first support roll 22 under water jet directed from the jet means 23, then fully treated on the second support roll 25 under water streams directed from the respective jet means 26 and simultaneously provided with the apertures as the respective projections 31 distribute the fibres aside. A back pressure of water stream is preferably selected in a range from 20 to 100 kg/cm$^2$. At a back pressure less than 20 kg/cm$^2$, a sufficient energy will not be obtained to achieve a desired fibre entanglement effect and both the efficiency and the strength of such fibre entanglement will be inadequate. At a back pressure higher than 100 kg/cm$^2$, the cost will become too high to be commercially reasonable and a texture of the fibrous web 30 will be easily disturbed. Water quantity is preferably selected in a range from 0.5 to 20 l/m$^2$. Water quantity less than 0.5 l/m$^2$ will be unable to provide sufficient efficiency and strength of fibre entanglement. Depending on the jet pressure, and diameter as well as number of orifices arranged in the water jet means 23, 26, even with a water quantity of 20 l/m$^2$ or higher, neither the efficiency nor the strength of fibre entanglement could be improved in proportion to such water quantity and, in consequence, such a level of water quantity will merely result in an economical disadvantage.

The manner in which the individual fibres are fused together to form the second layer 14 of the non-woven fabric as the facing according to the present invention is well known to those skilled in the art and will not be described in details.

(EXAMPLES)

Various examples are listed in Table 1.

Table 2 indicates properties of the examples as listed in Table 1 together with properties of controls.

Control 1 is the facing utilized by the applicant in a disposable diaper. This is the non-woven fabric formed by fibre entanglement treatment under high velocity water jet and comprising 50% by weight of 1.5 d×51 mm rayon fibres and 50% by weight of 1.4 d×44 mm polyester fibres. This non-woven fabric has a basic weight of 30 g/m$^2$.

Control 2 is the facing utilized by A company on disposable diaper manufactured by this company. This is made of 25 g/m$^2$ polyethylene film provided with a plurality of apertures with 0.5 mm$\phi$, 1 mm spacing and 20% aperture ratio.

The properties listed in Table 2 were determined by testing procedures as set forth below:

(1) Permeability

Sample (facing) was laid on top of an absorbent body made of cotton-like woody pulp and then 5 ml of artificial urine was poured down from a beaker at once over the sample. Seconds taken for complete permeation of the sample were counted.

(2) Rewet property

Sample was placed on top of an absorbent made of 100 cm$^2$ cotton-like woody pulp, then artificial urine was poured down from a burette over the sample by a quantity 5-times a weight of the absorbent body, there-after artificial skin sheet of rubber was laid on the sample and finally a weighing plate of 100 cm² and 7 kg was put on this assembly. After 3 minutes have elapsed, the weighing plate was removed and a quantity of artificial urine clinging to the artificial skin sheet was measured.

(3) Dry feel property

The sample after said rewet property was determined was touched by hand and a wetness remaining thereon was tested.

TABLE 1

| | First Layer | | | | Second Layer | | |
|---|---|---|---|---|---|---|---|
| Example | Fibre Type | Aperture area (mm²) | Aperture Ratio (%) | B.W. (g/m²) | Fibre Type | B.W. (g/m²) | Both Layers were combined By |
| 1 | PET 0.7 d × 38 mm (100%) | 0.295 | 20 | 25 | Hydrophilic nature imparted PET 1.5 d × 51 mm (100%) | 15 | Water Jet Treatment |
| 2 | PET 0.7 d × 38 mm (100%) | 2.64 | " | " | Hydrophilic nature imparted PET 1.5 d × 51 mm (100%) | " | " |
| 3 | PET 0.7 d × 38 mm (100%) | 10.60 | " | " | Hydrophilic nature imparted PET 1.5 d × 51 mm (100%) | " | " |
| 4 | PET 0.7 d × 38 mm (100%) | 29.5 | " | " | Hydrophilic nature imparted PET 1.5 d × 51 mm (100%) | " | " |
| 5 | PET 0.7 d × 38 mm (100%) | 2.64 | 10 | " | Hydrophilic nature imparted PET 1.5 d × 51 mm (100%) | " | " |
| 6 | PET 0.7 d × 38 mm (100%) | 2.64 | 30 | " | Hydrophilic nature imparted PET 1.5 d × 51 mm (100%) | " | " |
| 7 | PET 0.7 d × 38 mm (100%) | 2.64 | 50 | " | Hydrophilic nature imparted PET 1.5 d × 51 mm (100%) | " | " |
| 8 | PET 0.7 d × 38 mm (100%) | 2.64 | 70 | " | Hydrophilic nature imparted PET 1.5 d × 51 mm (70%) Low m.p. PET 3 d × 51 mm (30%) | " | Heat Fusion Treatment |
| 9 | PET 1.4 d × 44 mm (70%) Hydrophilic nature imparted PET 1.5 d × 51 mm (30%) | 2.64 | " | " | Hydrophilic nature imparted PET 1.5 d × 51 mm (70%) Low m.p. PET 3 d × 51 mm (30%) | " | Water Jet Treatment |

TABLE 2

| | Permeability | Rewet Property | Dry Feel Property |
|---|---|---|---|
| Example | | | |
| 1 | 15 sec | 5 mg/100 cm² | A |
| 2 | Shorter than 1 sec | 12 | A |
| 3 | Shorter than 1 sec | 15 | C |
| 4 | Shorter than 1 sec | 24 | C |
| 5 | 7 sec | 6 | B |
| 6 | Shorter than 1 sec | " | B |
| 7 | Shorter than 1 sec | 20 | C |
| 8 | Shorter than 1 sec | 13 | A |
| 9 | Shorter than 1 sec | 12 | A |
| Control | | | |
| 1 | Shorter than 1 sec | 30 | D |
| 2 | Shorter than 1 sec | 15 | A |

Note: A to D indicate better order, so that A is best whilst D is worst.

What is claimed is:

1. A facing cover for a body of absorbent material, said facing cover comprising a first apertured layer joined to a second unapertured layer,
    (a) said first layer composed of fibers entangled into a non-woven fabric and
        (1) having one surface which is adapted to be placed in contact with a person's body and the other surface being joined to one surface of said second layer,
        (2) being composed of 70–100% by weight of hydrophobic fibers and 0–30% by weight of hydrophilic fibers,
        (3) having a basic weight of at least 15 g/m², and
        (4) having a plurality of apertures therein, each of said apertures having an area within the range of 0.29–30 mm² and the overall area of said apertures being 10–50% of the total area, said apertures each being formed by the spreading apart of entangled fibers so as to leave an open area where there are no fibers, and
    (b) said second layer composed of fibers entangled into a non-woven fabric and
        (1) being composed of 50–100% by weight of hydrophilic fibers and 0–50% by weight of hydrophobic fibers, and
        (2) having a basic weight of 5–50 g/m²,
    (c) said first and second layers
        (1) each being formed by fiber entanglement treatment, and
        (2) being integrally combined with each other at their interface by the entanglement of the fibers in one layer with the fibers in the other layer.

2. A facing cover for a body of absorbent material, said facing cover comprising a first apertured layer joined to a second unapertured layer, (a) said first layer composed of fibers entangled into a non-woven fabric and
  (1) having one surface which is adapted to be placed in contact with a person's body and the other surface being joined to one surface of said second layer,
  (2) being composed of 70-100% by weight of hydrophobic fibers and 0-30% by weight of hydrophilic fibers,
  (3) having a basic weight of at least 15 g/m$^2$, and
  (4) having a plurality of apertures therein, each of said apertures having an area within the range of 0.29-30 mm$^2$ and the overall area of said apertures being 10-50% of the total area, said apertures each being formed by the physical spreading apart of entangled fibers so as to leave an open area where there are no fibers, and
(b) said second layer composed of fibers fused together into a non-woven fabric and
  (1) being composed of 50-100% by weight of hydrophilic fibers and 0-50% by weight of hydrophobic fibers,
  (2) having a basic weight of 5-50 g/m$^2$, and
  (3) being at least partially composed of thermofusive fibers which are fusing at a temperature of 90°-140° C., and
(c) said first and second layers being integrally combined with each other at their interface by the engagement of the fibers in one layer with the fibers in the other layer.

3. A facing cover according to claim 1, wherein fibers contained in said first layer have a denier of 0.2 to 2 and a density of 0.03 to 0.3 g/cm$^3$ while the fibers contained in said second layer have a denier of 0.7 to 15 and a density of 0.01 to 0.2 g/cm$^3$.

4. A process for making a facing cover for a body of absorbent material, said facing cover comprising a first apertured layer joined to a second unapertured layer, which process comprises the steps of:
(a) establishing a first layer composed of a non-woven fabric formed by fiber entanglement, said first layer of non-woven fabric
  (1) being composed of 70-100% by weight of hydrophobic fibers and 0-30% by weight of hydrophilic fibers, and
  (2) having a basic weight of 5-50 g/m$^2$, and
(b) forming a plurality of apertures in the product of step (a) by spreading apart the entangled fibers so as to leave an open space where there are no fibers, each of said apertures having an area within the range of 0.29-30 mm$^2$ and the overall area of said apertures being 10-50% of the total area of said first layer,
(c) forming a second layer composed of a non-woven fabric by fiber entanglement, said non-woven fabric
  (1) being composed of 50-100% by weight of hydrophilic fibers and 0-50% by weight of hydrophobic fibers, and
  (2) having a basic weight of 5-50 g/m$^2$, and
(d) integrally combining said first and second layers with each other at their interface by entangling the fibers in said first layer with the fibers in said second layer.

5. A process according to claim 4 wherein said first layer is produced by subjecting a fibrous web to high velocity water jet treatment on a support carrying thereon aperture formation elements distributed at predetermined spacings so as to achieve desired fiber entanglement and simultaneously fibers of said first fibrous web are distributed by said aperture formation elements aside so as to form said apertures through said first fibrous web, thus forming said first layer.

6. A process according to claim 5 wherein said second fibrous web is placed on said first layer and is subjected to high velocity water jet treatment so as to achieve the desired fiber entanglement in this second fibrous web as well as with fibers of said first layer, thus forming said second layer.

7. A process for making a facing cover for a body of absorbent material, said facing cover comprising a first apertured layer joined to a second unapertured layer, which process comprises the steps of
(a) establishing a first layer composed of a non-woven fabric by fiber entanglement, said first layer of non-woven fabric
  (1) being composed of 70-100% by weight of hydrophobic fibers and 0-30% by weight of hydrophilic fibers, and
  (2) having a basic weight of at least 15 g/m$^2$,
(b) forming a plurality of apertures in the product of step (a) by spreading apart the entangled fibers so as to leave an open space where there are no fibers, each of said apertures having an area within the range of 0.29-30 mm$^2$ and the overall area of said apertures being 10-50% of the total area,
(c) forming a second layer composed of a non-woven fabric
  (1) at least partially composed of hydrophobic and thermofusive fibers that are fusive at a temperature of 90°-140° C.,
  (2) having a basic weight of 5-50 g/m$^2$, and
(d) integrally combining said first and second layers with each other at their interface by heating said second layer after it has been placed on said first layer so as to obtain fiber fusion of the fibers in the second layer as well as with the fibers of said first layer.

8. A process according to claim 4 wherein the fibers of said first fibrous web have a denier of 0.2 to 2 while the fibers of said second fibrous web have a denier of 0.7 to 15.

9. A process according to claim 4 wherein said first layer and said second layer are treated so that these two layers respectively present densities of 0.03 to 0.3 g/cm$^3$ and 0.01 to 0.2 g/cm$^3$.

10. A process according to claim 7 wherein said first layer and said second layer are treated so that these two layers respectively present densities of 0.03 to 0.3 g/cm$^3$ and 0.01 to 0.2 g/cm$^3$.

* * * * *